US012673908B2

(12) United States Patent
Usui et al.

(10) Patent No.: US 12,673,908 B2
(45) Date of Patent: Jul. 7, 2026

(54) METHOD FOR PRODUCING FLUOROETHYLENE

(71) Applicant: DAIKIN INDUSTRIES, LTD., Osaka (JP)

(72) Inventors: Takashi Usui, Osaka (JP); Tomoyuki Iwamoto, Osaka (JP); Tsubasa Nakaue, Osaka (JP); Yuzo Komatsu, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 848 days.

(21) Appl. No.: 17/990,961

(22) Filed: Nov. 21, 2022

(65) Prior Publication Data

US 2023/0101465 A1 Mar. 30, 2023

Related U.S. Application Data

(63) Continuation of application No. PCT/JP2021/019298, filed on May 21, 2021.

(30) Foreign Application Priority Data

May 22, 2020 (JP) ................................ 2020-089833

(51) Int. Cl.
*C07C 17/25* (2006.01)
*B01J 23/86* (2006.01)

(52) U.S. Cl.
CPC ............ *C07C 17/25* (2013.01); *B01J 23/868* (2013.01); *C07B 2200/09* (2013.01)

(58) Field of Classification Search
CPC ..... C07C 17/25; C07C 2200/09; C07C 17/23; C07C 21/18; B01J 23/868
See application file for complete search history.

(56) References Cited

U.S. PATENT DOCUMENTS

| | | | | |
|---|---|---|---|---|
| 6,232,513 | B1 | 5/2001 | Hub et al. | |
| 11,542,216 | B2 * | 1/2023 | Takakuwa ............ | C07C 17/383 |
| 2010/0107871 | A1 | 5/2010 | Mantkowski | |
| 2018/0290951 | A1 | 10/2018 | Tomiyori et al. | |
| 2021/0253502 | A1 | 8/2021 | Usui et al. | |

FOREIGN PATENT DOCUMENTS

| | | |
|---|---|---|
| EP | 0 844 226 | 5/1998 |
| JP | 8-104656 | 4/1996 |
| JP | 2001-508786 | 7/2001 |
| JP | 2016-56132 | 4/2016 |
| WO | 2017/104829 | 6/2017 |
| WO | 2019/216175 | 11/2019 |

OTHER PUBLICATIONS

English language translation of International Search Report issued Aug. 10, 2021 in corresponding International (PCT) Patent Application No. PCT/JP2021/019298.
Raphaele Romelaer et al., "Thermal Isomerization of 1,1,2,2-Tetrafluoroethane (FC-134) to 1,1,1,2-Tetrafluoroethane (FC-134a) in the Presence of Hydrogen", Journal of American Chemical Society, 2001, vol. 123, No. 28, pp. 6773-6777.
English language Translation of International Preliminary Report on Patentability issued Nov. 17, 2022 in corresponding International (PCT) Patent Application No. PCT/JP2021/019298.
Extended European Search Report issued Jul. 8, 2024 in European Patent Application No. 21808582.7.

* cited by examiner

*Primary Examiner* — Jafar F Parsa
(74) *Attorney, Agent, or Firm* — Wenderoth, Lind & Ponack, L.L.P.

(57) ABSTRACT

An object of the present invention is to provide a method for efficiently obtaining fluoroethylene.
A method for producing at least one fluoroethylene compound selected from the group consisting of HFO-1132(Z/E), HFO-1132a, and HFO-1123, wherein the method comprises reacting at least one fluoroethane compound selected from the group consisting of HFC-134, HFC-134a, and HFC-125 with hydrogen ($H_2$).

12 Claims, No Drawings

METHOD FOR PRODUCING FLUOROETHYLENE

TECHNICAL FIELD

The present disclosure relates to a method for producing fluoroethylene.

BACKGROUND ART

Patent Literature 1 discloses a method for producing 1,2-difluoroethylene (HFO-1132), comprising reacting 1-chloro-1,2-difluoroethylene (HCFO-1122a) and hydrogen in a gas phase in the presence of a hydrogenated catalyst.

CITATION LIST

Patent Literature

PTL 1: JP2016-56132

SUMMARY

Item 1

A method for producing at least one fluoroethylene compound selected from the group consisting of (Z)- and/or (E)-1,2-difluoroethylene (HFO-1132(Z/E)), 1,1-difluoroethylene (HFO-1132a), and 1,1,2-trifluoroethylene (HFO-1123), the method comprising reacting at least one fluoroethane compound selected from the group consisting of
1,1,2,2-tetrafluoroethane (HFC-134),
1,1,1,2-tetrafluoroethane (HFC-134a), and
1,1,1,2,2-pentafluoroethane (HFC-125),
with hydrogen ($H_2$).

In the present specification, the following terms are described as below.

(Z)- and/or (E)-1,2-difluoroethylene: HFO-1132(Z/E)
HFO-1132 (E): Trans-1,2-difluoroethylene
HFO-1132 (Z): Cis-1,2-difluoroethylene
1,1,2,2-Tetrafluoroethane: HFC-134
1,1-Difluoroethylene: HFO-1132a
1,1,1,2-Tetrafluoroethane: HFC-134a
1,1,2-Trifluoroethylene: HFO-1123
1,1,1,2,2-Pentafluoroethane: HFC-125

Advantageous Effects of Invention

According to the present disclosure, fluoroethylene can be efficiently obtained.

DESCRIPTION OF EMBODIMENTS

An object of the present disclosure is to provide a means for solving the above problems. The present inventors conducted extensive research and found that a fluoroethylene compound of HFO-1132(Z/E), HFO-1132a, or HFO-1123 can be efficiently produced by respectively reacting a fluoroethane compound of HFC-134, HFC-134a, or HFC-125 with hydrogen ($H_2$); and that the above problems can be solved.

The present disclosure was accomplished based on the above findings, and as a result of further research. The present invention includes the following embodiments.

The production method of the present disclosure is a method for producing at least one fluoroethylene compound selected from the group consisting of HFO-1132(Z/E), HFO-1132a, and HFO-1123, and the method comprises reacting at least one fluoroethane compound selected from the group consisting of HFC-134, HFC-134a, and HFC-125 with hydrogen ($H_2$).

The production method of the present disclosure is preferably a method for producing HFO-1132(Z/E), comprising reacting HFC-134 with hydrogen ($H_2$).

The production method of the present disclosure is preferably a method for producing HFO-1132a, comprising reacting HFC-134a with hydrogen ($H_2$).

The production method of the present disclosure is preferably a method for producing HFO-1123, comprising reacting HFC-125 with hydrogen ($H_2$).

The production method of the present disclosure is a method in which the fluoroethane compound (raw material compound) of HFC-134, HFC-134a, or HFC-125 is reacted with hydrogen ($H_2$) to generate a carbene species by thermal decomposition, followed by a coupling reaction, thus respectively producing HFO-1132(Z/E), HFO-1132a, or HFO-1123 (target compound).

The carbene species generated by thermal decomposition are different between HFC-134, HFC-134a, and HFC-125. The thermal decomposition of HFC-134 produces a CFH carbene. The thermal decomposition of HFC-134a produces a $CH_2$ carbene and a $CF_2$ carbene. The thermal decomposition of HFC-125 produces a $CF_2$ carbene and a CFH carbene.

In the production method of the present disclosure, the reaction is preferably performed in a gas-phase flow process.

In the production method of the present disclosure, the reaction is preferably performed at a temperature of 400° C. or more.

In the production method of the present disclosure, the reaction is preferably performed by using hydrogen ($H_2$) in an amount of 0.1 to 10 mol per mol of the raw material compound (HFC-134, HFC-134a, or HFC-125) (molar ratio of $H_2$/raw material compound).

In the production method of the present disclosure, the reaction is preferably performed using a metal catalyst.

According to the production method of the present disclosure, the fluoroethylene compound (target compound) of HFO-1132(Z/E), HFO-1132a, or HFO-1123 can be respectively produced from the fluoroethane compound of HFC-134, HFC-134a, or HFC-125 (raw material compound) by a one-step (one-pot synthesis).

In the production method of the present disclosure, the HFO-1132(Z/E), HFO-1132a, or HFO-1123 (target compound) can be efficiently produced from inexpensive HFC-134, HFC-134a, or HFC-125 (raw material compound), respectively.

1. Raw Material Compound

The production method of the present disclosure is a process for respectively producing a fluoroethylene compound of HFO-1132(Z/E), HFO-1132, or HFO-1123 (target compound) in the presence of hydrogen ($H_2$) by the thermal decomposition of a fluoroethane compound of HFC-134, HFC-134a, or HFC-125 (raw material compound). In the production method of the present disclosure, the thermal decomposition produces a carbene species as a precursor of HFO-1132(Z/E), HFO-1132a, or HFO-1123.

The raw material compounds used in the production method of the present disclosure are HFC-134, HFC-134a, and HFC-125. Such halogenated ethanes are widely used for applications, such as refrigerants, solvents, foaming agents, and propellants, and are generally available.

2. Step of Reacting Raw Material Compound with Hydrogen ($H_2$)

The production method of the present disclosure is a method for respectively producing a fluoroethylene compound of HFO-1132(Z/E), HFO-1132a, or HFO-1123 (target compound) by the thermal decomposition of the fluoroethane compound (raw material compound) of HFC-134, HFC-134a, or HFC-125 in the presence of hydrogen ($H_2$). In the production method of the present disclosure, the thermal decomposition produces a carbene species as a precursor of the target compound.

In the present disclosure, the target compound HFO-1132 (Z/E) can be preferably produced when HFC-134 is used as a raw material compound. In the present disclosure, the target compound HFO-1132a can be preferably produced when HFC-134a is used as a raw material compound. In the present disclosure, the target compound HFQ-1123 can be preferably produced when HFC-125 is used as a raw material compound.

The method for producing HFO-1132 (Z/E) comprises reacting HFC-134 and hydrogen ($H_2$).

The method for producing HFO-1132a comprises reacting HFC-134a and hydrogen ($H_2$).

The method for producing HFO-1123 comprises reacting HFC-125 and hydrogen (NH).

The step of reacting the raw material compound and hydrogen ($H_2$) in the present disclosure is preferably performed in a gas phase, and more preferably in a gas-phase flow process. The production method of the present disclosure is particularly preferably performed in a gas-phase continuous flow process by using a fixed-bed reactor. The reaction performed in a gas-phase continuous flow process can simplify the equipment, operations, etc., and is also economically advantageous.

Catalyst

The step of reacting a raw material compound and hydrogen ($H_2$) in the present disclosure is preferably performed in the presence of a catalyst in a gas phase.

The catalyst used in this step is preferably activated carbon and/or a metal catalyst.

The metal catalyst is at least one metal catalyst selected from the group consisting of chromium oxide, fluorinated chromium oxide, chromium fluoride, copper chromium oxide, fluorinated copper chromium oxide, aluminum oxide, fluorinated aluminum oxide, aluminum fluoride, iron oxide, fluorinated iron oxide, iron fluoride, nickel oxide, fluorinated nickel oxide, nickel fluoride, copper oxide, fluorinated copper oxide, magnesium oxide, fluorinated magnesium oxide, and magnesium fluoride.

Of the metal catalysts, it is more preferred to use chromium oxide, fluorinated chromium oxide, chromium fluoride, copper chromium oxide, fluorinated copper chromium oxide, aluminum oxide, fluorinated aluminum oxide, or aluminum fluoride, from the standpoint of raising the conversion rate of the reaction.

In this step, when bringing the raw material compound into contact with a catalyst in a gas phase, it is preferable to bring the raw material compound into contact with the catalyst in a solid form (solid phase).

In this step, the catalyst may be in the form of a powder; however, the form of a pellet is preferred for the reaction in a gas-phase continuous flow process.

The specific surface area ("BET specific surface area" below) of the catalyst according to the BET theory is typically 10 to 3,000 $m^2/g$, preferably 10 to 400 $m^2/g$, more preferably 20 to 375 $m^2/g$, and still more preferably 30 to 350 $m^2/g$. A catalyst having a BET specific surface area within these numerical ranges does not have an overly low particle density, thus making it possible to obtain the target compound at a high selectivity. Such a catalyst can also increase the conversion rate of the raw material compound.

Activated carbon for use as a catalyst is preferably powdered activated carbon of crushed charcoal, briquette, granular charcoal, spherical charcoal, or the like. The powdered activated carbon for use preferably has a particle size of 4 mesh (4.76 mm) to 100 mesh (0.149 mm) in a JIS test.

The metal catalyst for use is preferably supported on a carrier. Examples of carriers include carbon, alumina ($Al_2O_3$), zirconia ($ZrO_2$), silica ($SiO_2$), and titania ($TiO_2$). The carbon for use includes activated carbon, amorphous carbon, graphite, and diamond.

Temperature of Reaction

In the step of reacting the raw material compound and hydrogen ($H_2$) in the present disclosure, the lower limit of the reaction temperature is typically about 400° C., preferably about 500° C., and more preferably about 600° C., from the standpoint of more efficiently performing the reaction to obtain the target compound at a higher selectivity and suppressing a decrease in the conversion rate.

The upper limit of the reaction temperature is typically about 1,200° C., and preferably about 1,000° C., from the standpoint of more efficiently performing the reaction of the raw material compound with hydrogen ($H_2$) to obtain the target compound at a higher selectivity and suppressing a decrease in selectivity due to decomposition or polymerization of the reaction product.

The step of reacting the raw material compound and hydrogen ($H_2$) in the present disclosure is preferably performed in the range of about 400 to 1200° C.

Time Period of Reaction (In the Case of Absence of Catalyst)

In the step of reacting the raw material compound and hydrogen in the absence of a catalyst in the present disclosure, the reaction time can be defined as the contact time ($V/F_0$) [V: volume of reaction tube (cc), $F_0$: flow rate of raw material compound (cc/sec)]. By increasing the contact time, the conversion rate can be increased. On the other hand, by extending the contact time, the flow rate of the raw material compound can be decreased, which decreases production efficiency.

Accordingly, when the catalyst is not used, the contact time is preferably 5 sec to 300 sec, more preferably 10 sec to 200 sec, and still more preferably 15 sec to 150 sec from the standpoint of increasing the conversion rate of the raw material compound and reducing equipment costs. The contact time of the raw material compound refers to the residence time in which the raw material compound passes through a pipe that attains a reaction temperature.

(In the Case of Presence of Catalyst)

In the step of reacting the raw material compound and hydrogen ($H_2$) in the presence of a catalyst in the present disclosure, the reaction time can be defined by the contact time between the raw material compound and the catalyst ($W/F_0$) [W: weight of catalyst (g), $F_0$: flow rate of raw material compound (cc/sec)]. An increase in the contact time increases the conversion rate of the raw material compound. However, the increase in the contact time increases the amount of a catalyst, which requires larger equipment, or reduces the flow rate of the raw material compound; accordingly, the production is inefficient. Accordingly, when the catalyst is used, the contact time ($W/F_0$) between the raw material compound and the catalyst is preferably 5 g·sec/cc to 300 g·sec/cc, more preferably 10 g·sec/cc to 200 g·sec/cc, and still more preferably 15 g·sec/cc to 150 g·sec/cc from the standpoint of increasing the conversion rate of the raw material compound and reducing equipment costs. The contact time between the raw material compound and the catalyst refers to the time period during which the raw material compound and the catalyst are in contact with each other.

When the step of reacting the raw material compound and hydrogen ($H_2$) in the present disclosure is performed in a gas phase in the presence of a catalyst, by suitably adjusting the reaction temperature and reaction time (contact time) according to the catalyst, the target compound can be obtained with high selectivity.

Reaction Pressure

In the step of reacting the raw material compound and hydrogen ($H_2$) in the present disclosure, the reaction pressure is preferably −0.05 MPa to 2 MPa, more preferably −0.01 MPa to 1 MPa, and still more preferably ordinary pressure to 0.5 MPa from the standpoint of more efficiently performing the reaction. In the present disclosure, the pressure is a gauge pressure unless indicated otherwise.

In the reaction, the reactor in which the raw material compound and a catalyst (e.g., metal catalyst) are brought into contact with each other and reacted is not limited in terms of shape and structure as long as the reactor is resistant to temperature and pressure. Examples of reactors include vertical reactors, horizontal reactors, and multi-tube reactors. Examples of reactor materials include glass, stainless steel, iron, nickel, and iron nickel alloy.

Examples of Reaction

In the step of reacting the raw material compound and hydrogen ($H_2$) in the present disclosure, the reaction can be performed in flow mode in which a raw material compound is continuously added to a reactor, and a target compound is continuously taken out from the reactor, or the reaction can be performed in batch mode. Because a target compound remaining in the reactor can allow the reaction to further proceed, the reaction is preferably performed in flow mode. In the step of reacting a raw material compound and hydrogen ($H_2$), the reaction is performed in a gas phase, particularly preferably in a gas-phase continuous flow process by using a fixed-bed reactor. The reaction performed in a gas-phase continuous flow process can simplify the equipment, operation, etc., and is also economically advantageous.

The atmosphere in which the reaction is performed is preferably an atmosphere in which inert gas and/or hydrogen fluoride is present in addition to hydrogen ($H_2$) that is reacted with the raw material compound, from the standpoint of suppressing degradation of the catalyst (e.g., metal catalyst). The inert gas is preferably at least one member selected from the group consisting of nitrogen, helium, argon, and carbon dioxide. Of these inert gasses, nitrogen ($N_2$) is more preferable from the standpoint of reducing costs. The concentration of the inert gas is preferably 0 to 99 mol % of the gas component introduced into the reactor.

After completion of the reaction, a purification treatment can be optionally performed in accordance with an ordinary method.

Amount of Hydrogen (Molar Ratio of $H_2$/Raw Material Compound)

The amount of hydrogen ($H_2$) in the step of reacting the raw material compound and hydrogen ($H_2$) in the present disclosure is not limited. In the present disclosure, the amount of hydrogen (H) is preferably 0.1 to 10 mol (molar ratio of $H_2$/raw material compound), and more preferably 0.5 to 2 mol (molar ratio of $H_2$/raw material compound) per mole of the raw material compound (HFC-134, HFC-134a, or HFC-125). In the present disclosure, thermal decomposition of the raw material compound in the presence of hydrogen ($H_2$) produces a carbene species as a precursor, thus producing HFO-1132(Z/E), HFO-1132a, or HFO-1123 (target compound) with high conversion rate (yield) and high selectivity.

Step of Recycling

In the present disclosure, in order to collect a composition with a higher proportion of a fluoroethylene compound of HFO-1132(Z/E), HFO-1132a, or HFO-1123 (target compound), a fluoroethane compound of HFC-134, HFC-134a, or HFC-125 (raw material compound) can be collected and recycled to the reaction after the step of reacting the raw material compound and hydrogen ($H_2$).

The present disclosure preferably comprises, after the step of reacting the raw material compound and hydrogen ($H_2$), the step of collecting the fluoroethylene compound of HFO-1132 (Z/E), HFO-1132a, or HFO-1123 (target compound) from the reaction product; and separating a stream mainly comprising HFC-134, HFC-134a, or HFC-125 (raw material compound), and a stream mainly comprising hydrogen fluoride (HF) generated after the reaction.

The present disclosure preferably comprises, after the above reaction, the step of recycling at least part of the separated stream mainly comprising the fluoroethane compound of HFC-134, HFC-134a, or HFC-125 to the above reaction to react with hydrogen (H) again. In the present disclosure, it is preferable to collect the fluoroethylene compound of HFO-1132(Z/E), HFO-1132a, or HFO-1123 (target compound) repeatedly, thus obtaining a composition in which the proportion of the target compound is more increased.

Method for Producing HFO-1132(Z/E) Comprising Step of Recycling

The method for producing HFO-1132 (Z/E) comprises the step of reacting HFC-134 and hydrogen ($H_2$), and preferably comprises, after the reaction, the step of collecting HFO-1132(Z/E) from the reaction product, and separating a stream mainly comprising HFC-134 and a stream mainly comprising hydrogen fluoride (HF) generated after the reaction; and the step of recycling at least part of the stream mainly comprising HFC-134 to the reaction to react with hydrogen ($H_2$) again.

Method for Producing HFO-1132a Comprising Step of Recycling

The method for producing HFO-1132a comprises the step of reacting HFC-134a and hydrogen ($H_2$), and preferably comprises, after the reaction, the step of collecting HFO-1132a from the reaction product, and separating a stream mainly comprising HFC-134a and a stream mainly comprising hydrogen fluoride (HF) generated after the reaction; and the step of recycling at least part of the stream mainly comprising HFC-134a to the reaction to react with hydrogen ($H_2$) again.

Method for Producing HFO-1123 Comprising Step of Recycling

The method for producing HFO-1123 comprises the step of reacting HFC-125 and hydrogen ($H_2$), and preferably comprises, after the reaction, the step of collecting HFO-1123 from the reaction product, and separating a stream mainly comprising HFC-125 and a stream mainly comprising hydrogen fluoride (HF) generated after the reaction; and the step of recycling at least part of the stream mainly comprising HFC-125 to the reaction to react with hydrogen (H) again.

3. Target Compound

The production method of the present disclosure is a process for producing the fluoroethylene compound (target compound) of HFO-1132(Z/E), HFO-1132a, or HFO-1123 by thermal decomposition of the fluoroethane compound of HFC-134, HFC-134a, or HFC-125 (raw material compound), respectively, in the presence of hydrogen ($H_2$). In the production method of the present disclosure, a carbene species is formed as a precursor of HFO-1132(Z/E), HFO-1132a, or HFO-1123 by the thermal decomposition.

The target compound of the production method of the present disclosure is a fluoroethylene compound of HFO-1132(Z/E), HFO-1132a, or HFO-1123. The fluoroethylene of HFO-1132(Z/E), HFO-1132a, or HFO-1123 produced by the production method of the present disclosure can be effectively used in various applications, including refrigerants, solvents, foaming agents, propellants, raw materials for resin products, organic synthesis intermediates, heat media, etc.

Item 1

A method for producing at least one fluoroethylene compound selected from the group consisting of (Z)- and/or (E)-1,2-difluoroethylene (HFO-1132(Z/E)), 1,1-difluoroethylene (HFO-1132a), and 1,1,2-trifluoroethylene (HFO-1123), the method comprising reacting at least one fluoroethane compound selected from the group consisting of 1,1,2,2-tetrafluoroethane (HFC-134), 1,1,1,2-tetrafluoroethane (HFC-134a), and 1,1,1,2,2-pentafluoroethane (HFC-125), with hydrogen ($H_2$).

Item 2

The production method according to Item 1, wherein the method is for producing (Z)- and/or (E)-1,2-difluoroethylene (HFO-1132(Z/E)), and comprises reacting 1,1,2,2-tetrafluoroethane (HFC-134) with hydrogen (H).

Item 3

The production method according to Item 2, comprising, after the reaction, collecting HFO-1132(Z/E) from a reaction product, and separating a stream mainly comprising HFC-134 and a stream mainly comprising hydrogen fluoride (HF) generated after the reaction; and recycling at least part of the stream mainly comprising HFC-134 to the reaction to react with hydrogen ($H_2$) again.

Item 4

The production method according to Item 1, wherein the method is for producing 1,1-difluoroethylene (HFO-1132a), and comprises reacting 1,1,1,2-tetrafluoroethane (HFC-134a) with hydrogen ($H_2$).

Item 5

The production method according to Item 4, comprising, after the reaction, collecting HFO-1132a from a reaction product, and separating a stream mainly comprising HFC-134a and a stream mainly comprising hydrogen fluoride (HF) generated after the reaction; and recycling at least part of the stream mainly comprising HFC-134a to the reaction to react with hydrogen ($H_2$) again.

Item 6

The production method according to Item 1, wherein the method is for producing 1,1,2-trifluoroethylene (HFO-1123), and comprises reacting 1,1,1,2,2-pentafluoroethane (HFC-125) with hydrogen ($H_2$).

Item 7

The production method according to Item 6, comprising, after the reaction, collecting HFO-1123 from a reaction product, and separating a stream mainly comprising HFC-125 and a stream mainly comprising hydrogen fluoride (HF) generated after the reaction; and recycling at least part of the stream mainly comprising HFC-125 to the reaction to react with hydrogen ($H_2$)

Item 8

The production method according to any one of Items 1 to 7, wherein the reaction is performed in a gas-phase flow process.

Item 9

The production method according to any one of Items 1 to 8, wherein the reaction is performed at a temperature of 400° C. or more.

Item 10

The production method according to any one of Items 1 to 9, wherein the reaction is performed in such a manner that the hydrogen ($H_2$) is used in an amount of 0.1 to 10 mol per mol of a raw material compound (molar ratio of $H_2$/raw material compound)

Item 11

The production method according to any one of Items 1 to 10, wherein the reaction is performed using a metal catalyst.

Item 12

The production method according to Item 11, wherein the metal catalyst is at least one metal catalyst selected from the group consisting of chromium oxide, fluorinated chromium oxide, chromium fluoride, copper chromium oxide, fluorinated copper chromium oxide, aluminum oxide, fluorinated aluminum oxide, aluminum fluoride, iron oxide, fluorinated iron oxide, iron fluoride, nickel oxide, fluorinated nickel oxide, nickel fluoride, copper oxide, fluorinated copper oxide, magnesium oxide, fluorinated magnesium oxide, and magnesium fluoride.

EXAMPLES

The present disclosure is explained with reference to Examples; however, the present disclosure is not limited to these Examples.

Example 1

Production of HFO-1132(Z/E) in the Absence of Catalyst

HFO-1132(Z/E) (target compound) was produced in a reactor (material: SUS316) by thermal decomposition of HFC-134 (raw material compound) in the presence of hydrogen ($H_2$).

HFC-134 (raw material compound): 3 mol %

Hydrogen ($H_2$): 3 mol %

Nitrogen gas (N) atmosphere: 94 mol %

Time of reaction: $V/F_0$=15 s

Reaction temperature: 500° C.

Reaction pressure: ordinal pressure

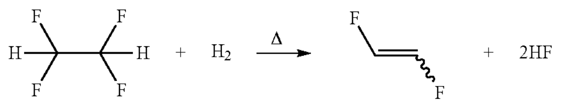

HFC-134 HFO-1132(Z/E)

TABLE 1

| Conversion rate (%) of raw material compound HFC-134 | Selectivity (%) | | | | | | |
|---|---|---|---|---|---|---|---|
| | HFO-1132 (E) | HFO-1132 (Z) | Methane | 4F | HFO-1141 | c-318 | HFC-143 |
| 0.29 | 10 | 33 | 14 | 2 | 2 | 32 | 7 |

4F: Tetrafluoroethylene (HFO-1114)

HFO-1141: Fluoroethylene c-318: Octafluorocyclobutane (perfluorocyclobutane)

HFC-143: 1,1,2-trifluoroethane

The "conversion rate" is the ratio (mol %) of the total molar amount of a compound other than the raw material compound, which is contained in a gas (=reaction gas) discharged from the reactor outlet, relative to the molar amount of the raw material compound supplied to the reactor (mol %).

The "selectivity" indicates the ratio (mol %) of the molar amount of the compound contained in a gas (=reaction gas) discharged from the reactor outlet to the total molar amount of compounds other than the raw material compound contained in the discharged gas (=reaction gas).

According to the production method of the present disclosure, HFC-134 is reacted with hydrogen ($H_2$) in gas flow mode to generate a CFH carbene, followed by coupling, thus synthesizing HFO-1132(Z/E).

The selectivity of HFO-1132(Z/E) was 43%.

As by-products, 4F, c-318 (dimer of 4F), and the like were produced.

It was evaluated that HFO-1132(Z/E) could be efficiently produced by the reaction of HFC-134 (raw material compound) and hydrogen ($H_2$) according to the production method of the present disclosure.

Examples 2 to 7

Production of HFO-1132(Z/E) in the Presence of Catalyst

A single pipe of a reactor (material: SUS316) was filled with a metal catalyst; and by the thermal decomposition of HFC-134 (raw material compound) in the presence of hydrogen ($H_2$), HFO-1132 (Z/E) (target compound) was produced.

Catalyst: copper chromium oxide (produced by Calsicat Company: S-93-346A E-103TU) 5 g Reaction temperature of Examples 2 to 6: 400° C.

Reaction temperature of Example 7: 500° C.

Reaction pressure: ordinal pressure

TABLE 2

| | Gas phase conditions | | | | | Raw material compound | Selectivity (%) | | | | | | | |
|---|---|---|---|---|---|---|---|---|---|---|---|---|---|---|
| Ex. | Reac. Temp. (° C.) | $N_2$ (mol %) | Raw material compound HFC-134 (mol %) | $H_2$ (mol %) | $W/F_0$ (g*s/ml) | HFC-134 Conversion rate (%) | HFO-1132 (E) | HFO-1132 (Z) | Methane | 4F | HFO-1141 | c-318 | HFC-143 | Others |
| 2 | 400 | 0 | 50 | 50 | 15 | 3.9 | 12 | 35 | 6 | 0 | 4 | 1 | 1 | 41 |
| 3 | 400 | 0 | 50 | 50 | 40 | 9.8 | 9 | 23 | 4 | 0 | 1 | 0 | 1 | 62 |
| 4 | 400 | 50 | 25 | 25 | 7.5 | 3.8 | 11 | 33 | 3 | 0 | 3 | 0 | 1 | 49 |
| 5 | 400 | 0 | 67 | 33 | 15 | 4.9 | 13 | 35 | 3 | 0 | 2 | 0 | 1 | 46 |
| 6 | 400 | 0 | 40 | 60 | 18 | 5.3 | 11 | 26 | 9 | 0 | 4 | 0 | 0 | 50 |
| 7 | 500 | 50 | 25 | 25 | 7.5 | 11 | 9 | 26 | 27 | 0 | 3 | 0 | 0 | 35 |

Ex.: Example

Reac. temp. (° C.): Reaction temperature (° C.)

Example 2

The reaction was performed in the presence of a copper chromium catalyst. Compared with the non-catalyst conditions (500° C.) of Example 1, the reaction proceeded at a low temperature (400° C.), and the conversion rate of the raw material compound HFC-134 was improved to 3.9%. The selectivity of the target compound HFO-1132(Z/E) was as high as 47%, which was higher than that of Example 1 in which the catalyst was absent. The column "Others" in Table 2 mainly includes hydrocarbon-based compounds such as ethane, ethylene, and propylene.

Example 3

The contact time $W/F_0$ was extended to 40 compared to Example 2 ($W/F_0$=15). The conversion rate of the raw material compound HFC-134 was improved to 9.8%. The selectivity of the target compound HFO-1132(Z/E) was 32%. Hydrocarbon-based compounds contained in the column "Others" were increased, suggesting that hydrogenation was progressed.

Example 4

Compared to Example 2 ($W/F_2$=15), the contact time $W/F_0$ was reduced to 7.5. Compared to Example 2 (HFC-134: 50, $H_2$: 50), the gas phase conditions were changed to $N_2$: 50, HFC-134: 25, and $H_2$: 25. The conversion rate of the raw material compound HFC-134 and the selectivity of the target compound HFO-1132 (Z/E) were similar to those in Example 2.

Example 5

Compared to Example 2 (HFC-134: 50, $H_2$: 50), the gas phase conditions were changed to HFC-134: 67 and $H_2$: 33. The conversion rate of the raw material compound HFC-134 and the selectivity of the target compound HFO-1132(Z/E) were similar to those in Example 2.

Example 6

Compared to Example 2 (HFC-134: 50 and $H_2$: 50), the gas phase conditions were changed to HFC-134: 40 and $H_2$: 60. The conversion rate of the raw material compound HFC-134 and the selectivity of the target compound HFO-1132(Z/E) were similar to those in Example 2.

Example 7

Compared to Example 4 (400° C.), the reaction temperature was increased to 500° C. Compared to Example 4, the conversion rate of the raw material compound HFC-134 was improved to 11%. Methane was the main product.

It was evaluated that HFO-1132(Z/E) could be more efficiently produced by reacting HFC-134 (raw material compound) and hydrogen ($H_2$) in the presence of a metal catalyst according to the production method of the present disclosure. By the use of a metal catalyst (preferably a copper chromium catalyst) in the reaction of HFC-134 (raw material compound) and hydrogen ($H_2$), it was understood that there is an effect of hydrogen reduction, and then chromium has an HF elimination effect as a Lewis acid.

The invention claimed is:

1. A production method, wherein the method is for producing (Z)- and/or (E)-1,2-difluoroethylene (HFO-1132 (Z/E)), and comprises reacting 1,1,2,2-tetrafluoroethane (HFC-134) with hydrogen ($H_2$), wherein the reaction is performed in the absence of catalyst, or in the presence of catalyst, in the case of presence of catalyst:

the catalyst is at least one catalyst selected from the group consisting of activated carbon, a metal catalyst, and a metal catalyst supported on a carrier, the metal catalyst is at least one metal catalyst selected from the group consisting of chromium oxide, fluorinated chromium oxide, chromium fluoride, copper chromium oxide, fluorinated copper chromium oxide, aluminum oxide, fluorinated aluminum oxide, aluminum fluoride, iron oxide, fluorinated iron oxide, iron fluoride, nickel oxide, fluorinated nickel oxide, nickel fluoride, copper oxide, fluorinated copper oxide, magnesium oxide, fluorinated magnesium oxide, and magnesium fluoride, the carrier supporting the metal catalyst is at least one carrier selected from the group consisting of carbon, alumina, zirconia, silica, and titania, the carbon is at least one carbon selected from the group consisting of activated carbon, amorphous carbon, graphite, and diamond.

2. The production method according to claim 1, comprising, after the reaction, collecting HFO-1132 (Z/E) from a reaction product, and separating a stream mainly comprising HFC-134 and a stream mainly comprising hydrogen fluoride (HF) generated after the reaction; and recycling at least part of the stream mainly comprising HFC-134 to the reaction to react with hydrogen ($H_2$) again.

3. A production method, wherein the method is for producing 1,1-difluoroethylene (HFO-1132a), and comprises reacting 1,1,1,2-tetrafluoroethane (HFC-134a) with hydrogen ($H_2$).

4. The production method according to claim 3, comprising, after the reaction, collecting HFO-1132a from a reaction product, and separating a stream mainly comprising HFC-134a and a stream mainly comprising hydrogen fluoride (HF) generated after the reaction; and recycling at least part of the stream mainly comprising HFC-134a to the reaction to react with hydrogen ($H_2$) again.

5. The production method according to claim 1, wherein the reaction is performed in a gas-phase flow process.

6. The production method according to claim 1, wherein the reaction is performed at a temperature of 400° C. or more.

7. The production method according to claim 1, wherein the reaction is performed in such a manner that the hydrogen ($H_2$) is used in an amount of 0.1 to 10 mol per mol of a raw material compound (molar ratio of $H_2$/raw material compound).

8. The production method according to claim 3, wherein the reaction is performed using a metal catalyst.

9. The production method according to claim 8, wherein the metal catalyst is at least one metal catalyst selected from the group consisting of chromium oxide, fluorinated chromium oxide, chromium fluoride, copper chromium oxide, fluorinated copper chromium oxide, aluminum oxide, fluorinated aluminum oxide, aluminum fluoride, iron oxide, fluorinated iron oxide, iron fluoride, nickel oxide, fluorinated nickel oxide, nickel fluoride, copper oxide, fluorinated copper oxide, magnesium oxide, fluorinated magnesium oxide, and magnesium fluoride.

10. The production method according to claim 3, wherein the reaction is performed in a gas-phase flow process.

11. The production method according to claim 3, wherein the reaction is performed at a temperature of 400° C. or more.

12. The production method according to claim 3, wherein the reaction is performed in such a manner that the hydrogen ($H_2$) is used in an amount of 0.1 to 10 mol per mol of a raw material compound (molar ratio of $H_2$/raw material compound).

* * * * *